United States Patent
Pype et al.

(10) Patent No.: US 7,098,322 B2
(45) Date of Patent: Aug. 29, 2006

(54) CD40-INTERACTING AND TRAF-INTERACTING PROTEINS

(75) Inventors: Stefan M. C. Pype, Wilrijk (BE); Jacques E. F. Remacle, Ilannut (BE); Danny F. E. Huylebroeck, Liedekerke (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 77 days.

(21) Appl. No.: 10/757,745

(22) Filed: Jan. 15, 2004

(65) Prior Publication Data

US 2005/0101769 A1    May 12, 2005

Related U.S. Application Data

(60) Division of application No. 09/697,863, filed on Oct. 27, 2000, now Pat. No. 6,812,203, which is a continuation of application No. PCT/EP99/03025, filed on Apr. 28, 1999.

(30) Foreign Application Priority Data

Apr. 29, 1998 (EP) .................................. 98201392

(51) Int. Cl.
*C07H 21/02* (2006.01)
(52) U.S. Cl. .................. 536/23.1; 435/69.1; 435/320.1; 530/351
(58) Field of Classification Search ................ 536/23.1; 435/69.1, 320.1; 530/351
See application file for complete search history.

(56) References Cited

U.S. PATENT DOCUMENTS

| | | | | |
|---|---|---|---|---|
| 6,379,951 | B1 * | 4/2002 | Reed et al. | 435/325 |
| 6,639,063 | B1 * | 10/2003 | Edwards et al. | 536/23.5 |

FOREIGN PATENT DOCUMENTS

| | | |
|---|---|---|
| JP | 11-75856 | 3/1999 |
| WO | WO 96/16665 | 6/1996 |
| WO | WO 96/18639 | 6/1996 |
| WO | WO 96/34473 | 9/1997 |
| WO | WO 97/94946 | 8/1998 |
| WO | WO 99/33869 | 7/1999 |
| WO | WO 99/55859 | 11/1999 |

OTHER PUBLICATIONS

Esparza et al. (2004) TRAF4 functions as an intermediate of GITR-induced NF-kappaB activation. Cell Mol. Life Sci. vol. 61, pp. 3087-3092.*
Force et al. (1997) Dominant negative mutants of TRAF3 reveal an important role for the coiled domains in cell death signaling by the lymphotoxin-beta receptor. J. Biol. Chem. vol. 272, pp. 30835-30840.*
Rothe et al. (19960 I-TRAF is a novel TRAF-interacting protein that regulates TRAF-mediated signal transduction. Proc. Natl. Acad. Sci. U S A. vol. 96 pp. 8241-8246.*
Mcwhirter et al. (1999) Structural and biochemical analysis of signal transduction by the TRAF family of adapter proteins. Cold Spring Harb. Symp. Quant. Biol. vol. 64, pp. 551-562.*
TNF Nomenclature Scheme (2000) "TNF receptor superfamilty" www.gene.ucl.ac.uk/nomenclature/genefamily/tnfrec2.html. pp. 1-2.*
Abstract XP-002115104, Pype et al., 3.13 "Identification of a Novel CD40 Interacting Protein", 1 page.
Abstract XP-002115105, Derwent Publications Ltd., "New Topoisomerase II-binding protein—useful as an anticancer agent", 1 page.
Hanissian et al. "Jak3 Is Associated with CD40 and is Critical for CD40 Induction of Gene Expression in B Cells", Immunity, vol. 5, pp. 379-387, Apr. 1997.
PCT International Search Report, PCT/EP99/03025, dated Sep. 30, 1999, 8 pages.
International Preliminary Examination Report, PCT/EP99/03025, dated Jul. 24, 2000.
Rothe et al., "A Novel Family of Putative Signal Transducers Associated with the Cytoplasmic Domain of the 75 kDa Tumor Necrosis Factor Receptor", Cell, vol. 78, pp. 681-692, Aug. 26, 1994.
Yang et al., "Daxx, a Novel Fas-Binding Protein That Activates JNK and Apoptosis", Cell, vol. 89, pp. 1067-1076, Jun. 27, 1997.
Gelibert et al., The involvement of multiple tumor necrosis factor receptor (TNFR)-associated factors in the signaling mechanisms of receptor activator of NF-kappaB, a member of the TNFR superfamily, 1998, J. Biol. Chem. pp. 34120-34127, vol. 273.
Honig, B, Protein folding: from the levinthal paradox to structure prediction, 1999, J. Mol. Biol., pp. 283-293, vol. 293.
Green et al., Identification of a novel vertebrate circadian clock-regulated gene encoding the protein nocturnin, 1996, Proc. Natl. Acad. Sci., pp. 14884-14888, vol. 93, USA.

* cited by examiner

*Primary Examiner*—Jon Weber
*Assistant Examiner*—Samuel W. Liu
(74) *Attorney, Agent, or Firm*—TraskBritt

(57) ABSTRACT

The present invention relates to novel proteins interacting with the cytoplasmic domain of CD40, which are useful in the treatment of CD40 and/or NF-κB related diseases. Surprisingly, these proteins do not show significant amino acid sequence identity with the members of tumor necrosis factor receptor associated factor (TRAF) family; and thus, offer the possibility to modulate the CD40 and/or NF-κB signaling pathway independently from interaction of TRAF with CD40.

3 Claims, 2 Drawing Sheets

CD40-INTERACTING AND TRAF-INTERACTING PROTEINS

CROSS-REFERENCE TO RELATED APPLICATIONS

This application is a divisional application of application U.S. Ser. No. 09/697,863, filed Oct. 27, 2000, now U.S. Pat. No. 6,812,203, which is a continuation of PCT International Application No. PCT/EP99/03025, filed on Apr. 28, 1999, designating the United States of America, and published in English as WO 99/55859 on Nov. 4, 1999, the contents of both of which are incorporated by this reference.

TECHNICAL FIELD

The invention relates to CD40 binding proteins, which can be used as modulators of the CD40 signaling pathway and/or the CD40-induced nuclear factor kappa B (NF-κB) activating pathway and thus useful in the treatment of CD40 related diseases (e.g., inflammatory diseases) and/or NF-κB related diseases and/or in the improvement of anti-tumor treatments. The current invention also relates to nucleic acid sequences coding for the CD40 interacting proteins (also called "TTRAP" ("TRAF and TNF receptor associated protein") for CD40 receptor associated protein). The invention further relates to the use of the polypeptides derived from these CD40 interacting proteins in the treatment of CD40 and/or NF-κB related diseases and/or cancer. Furthermore, the invention concerns pharmaceutical preparations comprising the CD40 interacting proteins or polypeptides derived from these proteins.

BACKGROUND

CD40 is a receptor of the tumor necrosis factor ("TNF")-receptor superfamily (Banchereau et al., 1994), which is expressed at the surface of B-cells, antigen presenting cells (APC), and several non-hematopoietic cells such as endothelial cells (Hollenbaugh et al., 1995), epithelial cells (Galy & Spits, 1992), fibroblasts (Fries et al., 1995) and keratinocytes (Gaspari et al., 1996). The ligand for CD40 (CD40L) occurs mainly on activated T-cells. Up to now the role of CD40 was mainly studied in the context of the T-cell APC/B-cell interaction (for a review, see Noelle, 1996). Amongst others, the CD40-CD40L interaction seems to be important for the T-cell mediated immunity and for primary and secondary humoral immune response. These findings were confirmed by experiments in mouse models showing that treatment with anti-CD40L antibodies resulted in blocking of the development of mouse equivalents of human autoimmune diseases such as arthritis (Durie et al. 1993), oophoritis (Griggs et al., 1996) and multiple sclerosis (Gerritse et al., 1996).

Activation and transduction through the CD40 pathway within this biological system is mainly responsible for B cell activation and the humoral immune response accordingly.

Apart from NF-κB, factors that can be activated by stimulation of CD40 are NF-AT (Francis et al., 1995) c-Jun, ATF-2 and IRF-1 (Karmann et al., 1996). All these factors play an important role in inflammation.

The CD40L induced signal transduction is, like TNF, mediated by the binding of TNF-Receptor Associated Factors (TRAF's) to the cytoplasmic domain of the receptor. Chaudhuri et al. (1997) demonstrated that, at least in human B cell lines, CD40 and TRAF2 are constitutively associated with each other, and that this association is inhibited by CD40 mediated signals. Apart from the binding with TRAF2, the cytoplasmic domain of CD40, which consists of 62 amino acids at positions 196–257 (mature human CD40-numbering according to Kashiwada et al., 1998), is known to associate with TRAF3, TRAF5, TRAF6 and Janus kinase 3. TRAF6 binds to the amino-terminal cytoplasmic tail of CD40 at positions 210–225, although it can not be excluded that full association of TRAF6 with CD40 may also require the carboxy-terminal part at positions 226–249 (Ishida et al., 1996). TRAF2, TRAF3 and TRAF5 bind to the carboxy-terminal CD40 cytoplasmic domain at positions 226–249 (Ishida et al., 1996).

Stimulation of CD40 results in activation of protein kinases, the mitogen-activated protein kinase and Janus kinase 3/signal transducer and activator of Transcription 3. Moreover, stimulation of CD40 mediates critical biological effects in B cell growth, survival and differentiation.

It is known that TRAF2 and TRAF5 play a role in NF-κB activation in signaling through CD40, as well as TNF-RI, TNF-RII, CD30 and lymphotoxin b receptor. TRAF6 participates in NF-κB activation signaled by CD40 and IL-1 receptor. In addition to these data, International Patent Applications WO 96/16665 and WO 96/28568 disclose a TRAF like protein that binds to the cytoplasmic domain of CD40.

DESCRIPTION OF THE INVENTION

We show herein that at least two other proteins exist which unexpectedly interact with the cytoplasmic domain of CD40. Even more surprisingly, neither of these proteins shows significant homology with any known CD40 interacting proteins. Further, no significant homology exists between the two proteins themselves. These proteins should, therefore, be considered as two new classes of CD40 interacting proteins.

The present invention, thus, concerns an isolated functional protein capable of interacting with the cytoplasmic domain of CD40 and/or other receptors of the TNF receptor superfamily such as CD30 or TNF receptor II, wherein the protein has no homology to TRAF-proteins.

The invention also includes an isolated functional protein either comprising an amino acid sequence with 70–100% homology to the amino acid sequence depicted in SEQ ID NO:2 or either comprising an amino acid sequence with 70–100% homology to the amino acid sequence depicted in SEQ ID NO:4 or, in the alternative, comprising an amino acid sequence with 70–100% homology to the amino acid sequence depicted in SEQ ID NO:6.

More specifically, the functional protein comprises an amino acid sequence with 70–100% homology to the amino acids 54–362 of SEQ ID NO:2, even more specifically, the functional protein comprises an amino acid sequence with 70–100% homology to the amino acids 274–362 of SEQ ID NO:2 or in the alternative and/or comprising an amino acid sequence with 70–100% homology to the amino acids 2–245 of SEQ ID NO:6.

Furthermore, the invention also includes those proteins or peptides having 70–100% homology to, at least, any of the three peptides as depicted in SEQ ID NO:2 located between the residues 115–121, 145–153 and 347–352, respectively. The amino acid sequence of residue numbering 115–121 of SEQ ID NO:2 is SLITWNI, the amino acid sequence of residue numbering 145–153 of SEQ ID NO:2 is PDVI-FLQEV and the amino acid sequence of residue numbering 347–352 of SEQ ID NO:2 is FPSDHW.

"Homology," in this context, means identical or similar to the referenced sequence while straightforward replacements/modifications of any of the amino acids provided, are included as well. A homology search in this respect can be performed with the BLAST-P (Basic Local Alignment Search Tool), a program well known to those of skill in the art. For the corresponding nucleic acid sequence, homology is referred to the BLASTX and BLASTN programs known in the art.

The invention thus relates to a DNA sequence encoding a CD40 receptor associated protein or encoding an immunologically active and/or functional fragment of such a protein, selected from the group consisting of:
  (a) DNA sequences comprising a nucleotide sequence encoding a protein comprising the amino acid sequence as given in SEQ ID NO:2;
  (b) DNA sequences comprising a nucleotide sequence as given in SEQ ID NO:1;
  (c) DNA sequences hybridizing with the complementary strand of a DNA sequence as defined in (a) or (b) and encoding an amino acid sequence which is at least 70% identical to the amino acid sequence encoded by the DNA sequence of (a) or (b);
  (d) DNA sequences, the nucleotide sequence of which is degenerated as a result of the genetic code to a nucleotide sequence of a DNA sequence as defined in any one of (a) to (c); and
  (e) DNA sequences encoding a fragment of a protein encoded by a DNA sequence of any one of (a) to (d).

One embodiment of the invention is a protein with SEQ ID NO:2. Another embodiment of the invention is a protein with SEQ ID NO:4. A further embodiment of the invention concerns a protein with SEQ ID NO:6.

A further aspect of the invention is the use of the aforementioned proteins, or biologically active fragments thereof, to modulate and/or inhibit members of the TNF receptor superfamily such as CD40, CD30 or TNF-receptor II in their signaling activity and/or CD40-induced NF-κB activation and/or JUN-kinase activity.

The isolated functional protein according to the invention and/or a functional fragment thereof can be used to treat TRAF-related, CD40-related, NF-κB related and/or Jun (kinase) related diseases. Such diseases include atherosclerosis, arthritis, multiple sclerosis, systemic lupus erythematosis ("SLE") and/or graft rejection.

In addition, the isolated functional protein according to the invention and/or a functional fragment thereof can be used to sensitize tumor cells to anti-tumor treatments.

Another aspect of the invention is the use of aforementioned proteins or biologically active fragments thereof to screen for compounds that interfere in the interactions of the proteins or fragments with other protein components of the CD40, TRAF or NF-κB related signaling pathway.

The invention also relates to a method for identifying and obtaining an activator or inhibitor of CD40 receptor associated proteins comprising the steps of:
  (a) combining a compound to be screened with a reaction mixture containing the protein of the invention and a readout system capable of interacting with the protein under suitable conditions;
  (b) maintaining the reaction mixture in the presence of the compound or a sample comprising a plurality of compounds under conditions which permit interaction of the protein with the read out system; and
  (c) identifying or verifying a sample and compound, respectively, which leads to suppression or activation of the read out system.

As used herein, the term "read out system" means a DNA sequence which upon transcription and/or expression in a cell, tissue or organism provides for a scorable and/or selectable phenotype. Such read out systems are well known to those skilled in the art and comprise, for example, recombinant DNA molecules and marker genes as previously described herein.

The term "plurality of compounds" in a method of the invention is to be understood as a plurality of substances which may or may not be identical.

The compound or plurality of compounds may be comprised in, for example, samples, e.g., cell extracts from animals or microorganisms. Furthermore, the compound(s) maybe known in the art but hitherto not known to be capable of suppressing or activating CD-40 receptor associated interacting proteins. The reaction mixture may be a cell free extract or may comprise a cell or tissue culture. Suitable set ups for the method of the invention are known to the person skilled in the art and are, for example, generally described in Alberts et al., Molecular Biology of the Cell, ($3^{rd}$ ed. 1994). The plurality of compounds may be, e.g., added to the reaction mixture, culture medium or injected into the cell.

If a sample containing a compound or a plurality of compounds is identified in the method of the invention, then it is either possible to isolate the compound from the original sample identified as containing the compound capable of suppressing or activating CD40 receptor associated proteins, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably, the sample comprises substances of similar chemical and/or physical properties, and most preferably the substances are identical. The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879–880; Hupp, Cell 83 (1995), 237–245; Gibbs, Cell 79 (1994), 193–198 and references cited supra).

Another aspect of the invention involves DNA molecules, also called nucleic acid sequences, encoding for the aforementioned proteins, preferably a nucleic acid sequence with 70–100% homology to the DNA sequence depicted in SEQ ID NO:1 and/or a nucleic acid sequence with 70–100% homology to the DNA sequence depicted in SEQ ID NO:3 or, in the alternative, a nucleic acid sequence with 70–100% homology to the DNA sequence depicted in SEQ ID NO:5.

"Homology," in this context, means that the respective nucleic acid molecules or encoded proteins are functionally and/or structurally equivalent. The nucleic acid molecules that are homologous to the nucleic acid molecules described above and that are derivatives of the nucleic acid molecules are, for example, variations of the nucleic acid molecules which represent modifications having the same biological function, in particular encoding proteins with the same or substantially the same biological function. They may be naturally occurring variations, such as sequences from other varieties or species, or mutations. These mutations may occur naturally or may be obtained by mutagenesis techniques. The allelic variations may be naturally occurring allelic variants as well as synthetically produced or genetically engineered variants.

The proteins encoded by the various derivatives and variants of the above-described nucleic acid molecules have similar common characteristics, such as biological activity, molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc.

A further embodiment of the invention concerns a method for identifying and obtaining CD40 receptor associated proteins comprising the LexA two-hybrid system wherein LeXA DNA-binding domain as a bait and a HeLa cell fusion library in plasmid pJG45 as prey is used. A DNA sequence encoding a CD40 receptor associated protein obtainable by the method belongs to the invention as well.

The present invention also relates to vectors, particularly plasmids, cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y.

Alternatively, the nucleic acid molecules and vectors of the invention can be reconstituted into liposomes for delivery to target cells.

In a preferred embodiment, the nucleic acid molecule present in the vector is operably linked to a control sequence or control sequences that allow for the expression of the nucleic acid molecule in prokaryotic and/or eukaryotic cells.

The term "control sequence" refers to regulatory DNA sequences which are necessary to affect the expression of coding sequences to which they are ligated. The nature of such control sequences differs depending upon the host organism. In procaryotes, control sequences generally include promoter, ribosomal binding site, and terminators. In eucaryotes generally, control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. If the control sequence is a promoter, a double-stranded nucleic acid is used.

Thus, the vector of the invention is preferably an expression vector. An "expression vector" is a construct that can be used to transform a selected host cell and provides for expression of a coding sequence in the selected host. Expression vectors can, for instance, be cloning vectors, binary vectors or integrating vectors. Expression comprises transcription of the nucleic acid molecule preferably into a translatable mRNA. Regulatory elements ensuring expression in prokaryotic and/or eukaryotic cells are well known to those skilled in the art.

The present invention furthermore relates to host cells comprising a vector as described above or a nucleic acid molecule according to the invention wherein the nucleic acid molecule is foreign to the host cell.

By "foreign" it is meant that the nucleic acid molecule is either heterologous with respect to the host cell, this means derived from a cell or organism with a different genomic background, or is homologous with respect to the host cell but located in a different genomic environment than the naturally occurring counterpart of the nucleic acid molecule. This means that, if the nucleic acid molecule is homologous with respect to the host cell, it is not located in its natural location in the genome of the host cell, in particular it is surrounded by different genes. In this case, the nucleic acid molecule may be either under the control of its own promoter or under the control of a heterologous promoter. The vector or nucleic acid molecule according to the invention which is present in the host cell may either be integrated into the genome of the host cell or it may be maintained in some form extra-chromasomally. In this respect, it is also to be understood that the nucleic acid molecule of the invention can be used to restore or create a mutant gene via homologous recombination (Paszkowski (ed.), Homologous Recombination and Gene Silencing in Plants, Kluwer Academic Publishers (1994)).

The host cell can be any prokaryotic or eukaryotic cell, such as bacterial, insect, fungal, plant or animal cells. Preferred fungal cells are, for example, those of the genus *Saccharomyces*, in particular those of the species *S. cerevisiae*.

The invention also includes a method for preparing CD40 receptor associated proteins which method comprises the cultivation of host cells according to the invention which, due to the presence of a vector or a nucleic acid molecule according to the invention, are able to express such a protein, under conditions which allow expression of the protein and recovering of the so-produced protein from the culture.

The present invention furthermore relates to proteins encoded by the nucleic acid molecules according to the invention or produced or obtained by the herein described methods, and to functional and/or immunologically active fragments of such CD40 receptor associated proteins. The proteins and polypeptides of the present invention are not necessarily translated from a designated nucleic acid sequence; the polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art. In this context, it is also understood that the proteins according to the invention may be further modified by conventional methods known in the art. By providing the proteins according to the present invention it is also possible to determine fragments which retain biological activity, namely the mature, processed form. This allows the construction of chimeric proteins and peptides comprising an amino sequence derived from the protein of the invention, which is crucial for its binding activity. The other functional amino acid sequences may be either physically linked by, e.g., chemical means to the proteins of the invention or may be fused by recombinant DNA techniques well known in the art.

Furthermore, the present invention relates to antibodies specifically recognizing a CD40 receptor associated protein according to the invention or parts, i.e., specific fragments or epitopes of such a protein. The antibodies of the invention can be used to identify and isolate other CD40 receptor associated proteins and genes in any organism. These antibodies can be monoclonal antibodies, polyclonal antibodies or synthetic antibodies as well as fragments of antibodies, such as Fab, Fv or scFv fragments, etc. Monoclonal antibodies can be prepared, for example, by the techniques as originally described in Köhler and Milstein, Nature 256 (1975),495, and Galfré, Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual," CSH Press, Cold Spring Harbor, 1988. These antibodies can be used, for example, for the immunoprecipitation and immunolocalization of proteins according to the invention as well as for the monitoring of the synthesis of such proteins, for example, in recombinant organisms and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97–105; Malmborg, J. Immunol. Methods 183 (1995), 7–13). In many cases, the binding phenomena of antibodies to antigens is equivalent to other ligand/anti-ligand binding.

The invention also relates to a diagnostic composition comprising at least one of the aforementioned nucleic acid molecules, vectors, proteins, antibodies or compounds and optionally suitable means for detection.

The diagnostic compositions may be used for methods for detecting expression of related CD40 receptor associated proteins by detecting the presence of the corresponding mRNA which comprises isolation of mRNA from a cell and contacting the mRNA so obtained with a probe comprising a nucleic acid probe as described above under hybridizing conditions, detecting the presence of mRNA hybridized to the probe, and thereby detecting the expression of the protein in the cell. Further methods of detecting the presence of a protein according to the present invention comprises immuno-techniques well known in the art, for example, enzyme linked immunosorbent assay.

The invention also relates to a pharmaceutical composition comprising one or more of the above mentioned proteins or fragments in a biologically active amount for the treatment of CD40, TRAF and/or NF-κB related diseases such as atherosclerosis, arthritis, multiple sclerosis, systemic lupus erythematosis, graft rejection and the like.

In another aspect, the present invention relates to a pharmaceutical composition comprising one or more compounds obtainable by the above-mentioned screening method for the treatment of CD40, TRAF and/or NF-κB related diseases such as atherosclerosis, arthritis, multiple sclerosis, systemic lupus erythematosis, graft rejection and the like.

DETAILED DESCRIPTION OF THE INVENTION

Definitions

Figure 1:
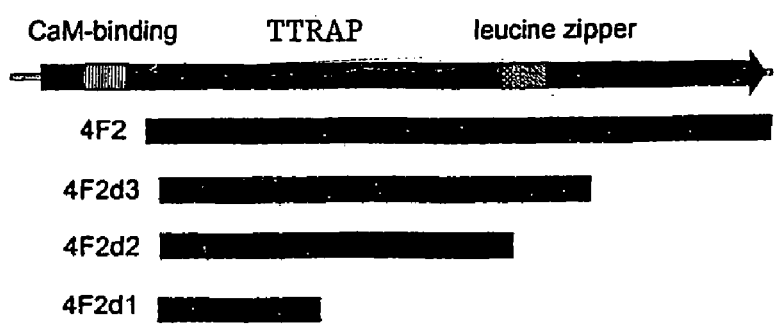
FIG. 1: Schematic representation of TTRAP (=CD40 receptor associated protein) and the deletion mutants of TTRAP used in two-hybrid assays. The deletion mutants consist of the following amino acids of the original TTRAP sequence: 54 to 362 (4F2), 54 to 273 (4F2d3), 54 to 236 (4F2d2) and 54 to 140 (4F2d1). (CaM=calcium calmodulin binding region.)

The following definitions are provided in order to further illustrate and define the meaning and scope of the various terms used in the current description.

As used herein, "homology to TRAF-proteins" means that the typical structural features found in the current TRAF proteins (TRAF1–TRAF6) are present. These features comprise a RING finger motif at the amino terminus followed by five or more zinc fingers and a so-called TRAF domain known to a person skilled in the art.

As used herein, "CD40," it is not to limit the scope to CD40 only, but also includes other receptors of the TNF receptor superfamily such as CD30 or TNF receptor II, unless indicated to the contrary.

The term "treatment" or "treating" or "treat" means any treatment of a disease in a mammal, including: (1) preventing the disease causing the clinical symptoms of the disease not to develop; (2) inhibiting the disease arresting the development of the clinical symptoms; and/or (3) relieving the disease causing the regression of clinical symptoms.

The term "effective amount" means a dosage sufficient to provide treatment for the disease state being treated. This will vary depending on the patient, the disease and the treatment being effected.

"Capable of interacting" means that a protein can form a complex with another protein, as can be measured using a yeast two-hybrid system, or with co-immunoprecipitation, or with equivalent systems known to people skilled in the art.

"Functional" protein or fragment means a protein or fragment that is capable to interact with the cytoplasmic part of CD40, or with another protein of the CD40 and/or NF-κB related pathway.

The "cytoplasmic part of CD40" means a part comprising the 62 carboxy terminal amino acids of human CD40 (amino acid 216–277; Stamenkovic et al. 1989), or the homologous mouse sequence, or another homologous sequence with a similar biological activity.

The term "expression" means the production of a protein or nucleotide sequence in the cell. However, the term also includes expression of the protein in a cell-free system. It includes transcription into an RNA product, post-transcriptional modification and/or translation to a protein product or polypeptide from a DNA encoding that product, as well as possible post-translational modifications. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesized and/or modified according to standard methods.

The terms "protein" and "polypeptide," as used herein, are interchangeable. "Polypeptide" refers to a polymer of amino acids (amino acid sequence) and does not refer to a specific length of the molecule. Thus, peptides and oligopeptides are included within the definition of polypeptide. This term also refers to or includes post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The terms "gene(s)," "polynucleotide," "nucleic acid sequence," "nucleotide sequence," "DNA sequence" or "nucleic acid molecule(s)," as used herein, refer to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, methylation, "caps" substitution of one or more of the naturally occurring nucleotides with an analog. Preferably, the DNA sequence of the invention comprises a coding sequence encoding the above defined CD40 receptor associated protein.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, recombinant nucleotide sequences or genomic DNA, while introns may be present as well under certain circumstances.

The term "functional fragment of a sequence" or "functional part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids.

Furthermore, folding simulations and computer redesign of structural motifs of the protein of the invention can be performed using appropriate computer programs (Olszewski, Proteins 25 (1996), 286–299; Hoffman, Comput. Appl. Biosci. 11 (1995), 675–679). Computer modeling of protein folding can be used for the conformational and energetic analysis of detailed peptide and protein models (Monge, J. Mol. Biol. 247 (1995), 995–1012; Renouf, Adv. Exp. Med. Biol. 376 (1995), 37–45). In particular, the appropriate programs can be used for the identification of interactive sites of the inventive protein, its receptor, its ligand or other interacting proteins by computer assisted searches for complementary peptide sequences (Fassina, Immunomethods 5 (1994), 114–120). Further, appropriate computer systems for the design of protein and peptides are described in the prior art, for example in Berry, Biochem. Soc. Trans. 22 (1994), 1033–1036; Wodak, Ann. N.Y. Acad. Sci. 501 (1987), 1–13; and Pabo, Biochemistry 25 (1986), 5987–5991. The results obtained from the above-described computer analysis can be used for, e.g., the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218–33224). For example, incorporation of easily available achiral $_c$W-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769–777). Superactive peptidomimetic analogues of small peptide hormones in other systems are described in the prior art (Zhang, Biochem. Biophys. Res. Commun. 224 (1996), 327–331). Appropriate peptidomimetics of the protein of the present invention can also be identified by the synthesis of peptidomimetic combinatorial libraries through successive amide alkylation and testing the resulting compounds, e.g., for their binding and immunological properties. Methods for the generation and use of peptidomimetic combinatorial libraries are described in the prior art, for example, in Ostresh, Methods in Enzymology 267 (1996), 220–234 and Dorner, Bioorg. Med. Chem. 4 (1996), 709–715.

Furthermore, a three-dimensional and/or crystallographic structure of the protein of the invention can be used for the design of peptidomimetic inhibitors of the biological activity of the protein of the invention (Rose, Biochemistry 35 (1996), 12933–12944; Rutenber, Bioorg. Med. Chem. 4 (1996), 1545–1558).

"Compound" means any chemical or biological compound, including simple or complex inorganic or organic molecules, peptides, peptido-mimetics, proteins, antibodies, carbohydrates or nucleic acids, that interferes with the interaction of a protein depicted in SEQ ID NO:2, SEQ ID NO:4, or SEQ ID NO:6 with a compound of the CD40 and/or NF-κB related pathway.

As used herein, the term "composition" refers to any composition such as a pharmaceutical composition comprising as an active ingredient a functional protein according to the present invention possibly in the presence of suitable excipients known to the skilled man and may thus be administered in the form of any suitable composition as detailed below by any suitable method of administration within the knowledge of a skilled man. The preferred route of administration is parenterally. In parenteral administration, the compositions of this invention will be formulated in a unit dosage injectable form such as a solution, suspension or emulsion, in association with a pharmaceutically acceptable excipient. Such excipients are inherently nontoxic and non-therapeutic. Examples of such excipients are saline, Ringer's solution, dextrose solution and Hank's solution. Non-aqueous excipients such as fixed oils and ethyl oleate may also be used. A preferred excipient is 5% dextrose in saline. The excipient may contain minor amounts of additives such as substances that enhance isotonicity and chemical stability, including buffers and preservatives.

The functional protein of the invention is administered at a concentration that is therapeutically effective to prevent allograft rejection, graft versus host disease ("GVHD"), allergy and autoimmune diseases. The dosage and mode of administration will depend on the individual. Generally, the compositions are administered so that the functional protein is given at a dose between 1 mg/kg and 10 mg/kg, more preferably between 10 mg/kg and 5 mg/kg, and most preferably between 0.1 and 2 mg/kg. Preferably, it is given as a bolus dose. Continuous short time infusion (during 30 minutes) may also be used. The compositions comprising the functional protein according to the invention may be infused at a dose between 5 and 20 mg/kg/minute, more preferably between 7 and 15 mg/kg/minute.

According to a specific case, the "therapeutically effective amount" of the functional protein according to the invention needed should be determined as being the amount sufficient to cure the patient in need of treatment or at least to partially arrest the disease and its complications. Amounts effective for such use will depend on the severity of the disease and the general state of the patient's health. Single or multiple administrations may be required depending on the dosage and frequency as required and tolerated by the patient.

With regard to the use of the functional protein of the present invention to prevent allograft rejection, it should be stressed that the proteins of the present invention or the compositions comprising the same may be administered before, during or after the organ transplantation as is desired from case to case. In case the protein or the compositions comprising the same are administered directly to the host, treatment will preferably start at the time of the transplantation and continue afterwards in order to prevent the activation and differentiation of host T cells against the major histocompatibility complex ("MHC") on the allograft. In case the donor organ is ex vivo perfused with the functional protein according to the invention or the compositions comprising the same, treatment of the donor organ ex vivo will start before the time of the transplantation of the donor organ in order to prevent the activation and differentiation of host T cells against the MHC on the allograft The invention is further explained by way of the following illustrative examples:

EXAMPLES

Example 1

Isolation of the CD40 Interacting Proteins

Yeast Two-hybrid Screening.

The two-hybrid assay was performed by the interaction trap cloning method, which is often referred to as the LexA two-hybrid system (Gyuris et al., 1993). The DNA encoding the cytoplasmic part of CD40 (62 amino acids, from residue 216 to 277, where the open reading frame ends, according to the sequence and numbering as given in Stamenkovic et al. (1989)) was generated by PCR and inserted into the EcoRI-SalI digested pEG202 vector (Gyuris et al., 1993), in frame with the LeXA DNA-binding domain (hereinafter the "bait plasmid"). Screening was performed using a HeLa cell fusion library in the plasmid pJG45 (hereinafter the "prey plasmid") obtained from the laboratory of R. Brent (Harvard Med. School, Boston, Mass., USA). Transformation of EGY48 yeast (MAT alpha, his3, trp1, ura3–52, leu2::pLeu2-LexAop6) with the prey plasmid, the bait plasmid and the p8op-LacZ (Clontech) reporter plasmid was performed by the Lithium Acetate transformation method (Gietz et al., 1995). The two-hybrid screening was conducted as described in the manual distributed by the laboratory of R. Brent (published in "Gene probes-A practical approach, Oxford University press").

Results of the Two-hybrid Screening.

Yeast containing bait plasmid and lacZ reporter plasmid was transformed with 20 microgram prey library plasmid and plated on glucose medium lacking tryptophan, histidine and uracil to select for the presence of all three plasmids. In total, approximately $1.5 \times 10^6$ colonies were obtained. The colonies were harvested and frozen at $-70°$ C. in a glycerol solution (65% v/v glycerol; 0.1 M $MgSO_4$, 25 mM Tris pH 7.4). From these stocks, $20 \times 10^6$ colony forming units were plated on galactose medium lacking leucine, tryptophan, histidine and uracil to screen for protein-protein interaction. Yeast colonies growing on the latter selective medium were further checked for interaction by screening for blue/white staining on medium containing X-gal and galactose. The colonies displaying the following phenotype were picked for further analysis: i) no growth on glucose containing medium which lacks leucine, ii) growth on galactose containing medium lacking leucine, iii) white on medium containing glucose and X-gal, and iv) blue on medium containing galactose and X-gal.

Plasmids were isolated from the yeast with the proper phenotype. Analysis of the obtained prey plasmids revealed that the entire screening had finally resulted in the isolation of three different cDNA inserts. Sequencing of the clones showed, in addition to a partial cDNA for TRAF3, two novel cDNA's, termed TTRAP and 4C4.

Isolation of the Full-length cDNA

Full-length human TTRAP cDNA was obtained by screening a HUVEC cDNA library with the TTRAP fragment as a probe. A cDNA of about 2 kb was isolated, with an open reading frame of 1086 nucleotides encoding for a protein of 362 amino acids (SEQ ID NO:2).

The mouse TTRAP homologue was obtained by screening the EST database and aligning the homologous sequences. Human and mouse TTRAP are approximately 65% identical and 70% similar on the amino acid level. The mouse sequence is shown in SEQ ID NO:3.

Example 2

Sequence Analysis of the cDNA's

Nucleotide sequence analysis was carried out using dye terminator mix and a 310 Genetic analyzer from Perkin Elmer. The nucleotide sequence of TTRAP is shown in SEQ ID NO:1 whereas the sequence of 4C4 is shown in SEQ ID NO:5.

The TTRAP sequence shows a low homology (30% similarity at amino acid level) with Nocturnin, a protein that is expressed in the photoreceptor of the eye of *Xenopus laevis* (Green and Beshare, 1996). The partial sequence of the mouse homologue of Nocturnin is known (Puech et al., 1997). Additionally, there is some homology with EST sequences (e.g., Genbank EST c23016, aa162513, aa571061, t87026, h45114, aa196281, h94108 and aa337396) and with the C-terminal part of the yeast transcription factor CCR4 (Malvar et al., 1992). Although these homologies are low, it is not excluded that a human homologue of these proteins would bind to the cytoplasmic domain of CD40.

It is interesting to note that, unexpectedly, TTRAP neither 4C4 show any significant homology with TRAF's or other proteins known to interact with CD40.

Example 3

Study of the Interaction of TTRAP Protein, 4C4 Protein and TTRAP Protein Fragments with Other Proteins Using a Yeast Two-hybrid Interaction Assay The potential binding of TTRAP to other proteins was assessed using a yeast two-hybrid assay. The experimental outline is similar to the one described for the two-hybrid screening. However, here the plasmids for bait, prey and lacZ reporter were transformed simultaneously into the EGY48 yeast strain. Positive interaction was determined either by the growth phenotype (growth on medium lacking leucine in the presence of galactose, and not in the presence of glucose) or by the blue/white staining on X-gal containing plates (blue colonies only on galactose containing plates, not on glucose containing plates). cDNA's for TRAF2 and for the cytoplasmic regions of CD30, CD40 and TNF-RII were generated by PCR using the pfu polymerase (Promega). PCR fragments encoding RIP, TRADD and FADD were cloned in pCDNA3 (Invitrogen, Carlsbad, Calif.). cDNA of TRAF3 was obtained from the laboratory of Dixit, Dept Pathol., Univ. Michigan Med. School, MI, USA. The color formation was evaluated as strong and fast (++), strong but slow (+), weak and slow (+/−), none (−) or not determined (nd).

The results for TTRAP protein and TTRAP fragments used are summarized in Table I and FIG. 1, respectively.

TABLE I

|  | TTRAP | 4F2 | 4F2d3 | 4F2d2 | 4F2d1 | 4C4 | — |
|---|---|---|---|---|---|---|---|
| CD40 | ++ | ++ | +/− | +/− | +/− | + | − |
| CD30 | ++ | ++ | +/− | +/− | +/− | + | − |
| TNF-RII | + | + | − | − | − | + | − |
| LMP-1 | − | − | nd | nd | nd | − | − |
| TRAF2 | + | + | nd | nd | nd | nd | − |
| TRAF3 | + | + | +/− | +/− | +/− | nd | − |
| RIP | ++ | ++ | +/− | +/− | +/− | nd | +/− |
| TRADD | + | nd | nd | nd | nd | nd | − |
| FADD | − | nd | nd | nd | nd | nd | − |
| 4F2 | ++ | ++ | − | − | − | + | − |
| 4C4 | ++ | ++ | − | − | − | + | − |

TTRAP, as well as the longest TTRAP fragment (aa 54–362), shows a strong interaction with CD40, CD30, RIP and with 4C4 and a weaker interaction with TNF-RII and TRAF3. Remarkably, TTRAP can also self-associate. TTRAP fragments, missing the C-terminal end (aa 274–362), show only a weak interaction.

Yeast transformed with TTRAP or 4F2 as a prey and TRAF2 as a bait gives a positive interaction phenotype similar to the one observed for TTRAP and TRAF3. This clearly indicates that TTRAP/4F2 also associates with TRAF2.

Because of the interaction of TTRAP with TRAF2 and 3 in two-hybrid assays in yeast, and with TRAF5 in co-immunoprecipitations from mammalian cells (see example 6) the conclusion is justified that TTRAP binds all other TRAFs as well. Deletion mutants of TRAFs are constructed to find out whether the region commonly denominated as the TRAF domain is responsible for the binding of the TRAFs to TTRAP. In a similar approach, deletion mutants of TTRAP are constructed to find out which region in the protein is required and sufficient for the interaction with TRAFs.

4C4 protein is interacting with CD40, CD30, TNF-RII, with the longest fragment of TTRAP and with a deletion mutant of TRAF3 which still contains the largest part of the TRAF domain (from aa 380 to the carboxy terminal end of the protein). A smaller form of 4C4 (from amino acid 2-amino acid 245 in SEQ ID NO:6) is also capable to interact with CD40.

Example 4

Expression Pattern of TTRAP and 4C4

Figure 2:
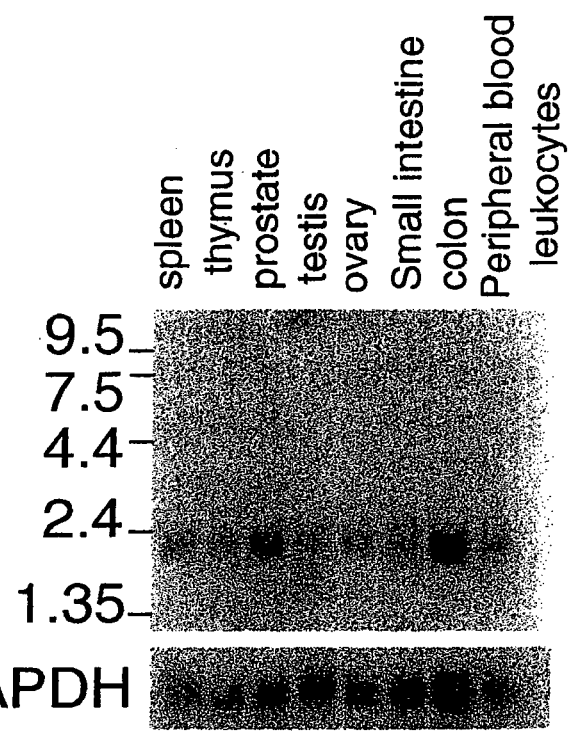
FIG. 2: Northern blot analysis of (a) human tissue, using a human TTRAP probe; (b) adult mouse tissue, using a mouse TTRAP probe; (c) embryonic mouse tissue, using a mouse TTRAP probe. The hybridization of GAPDH is used as a control.
Figure 2:
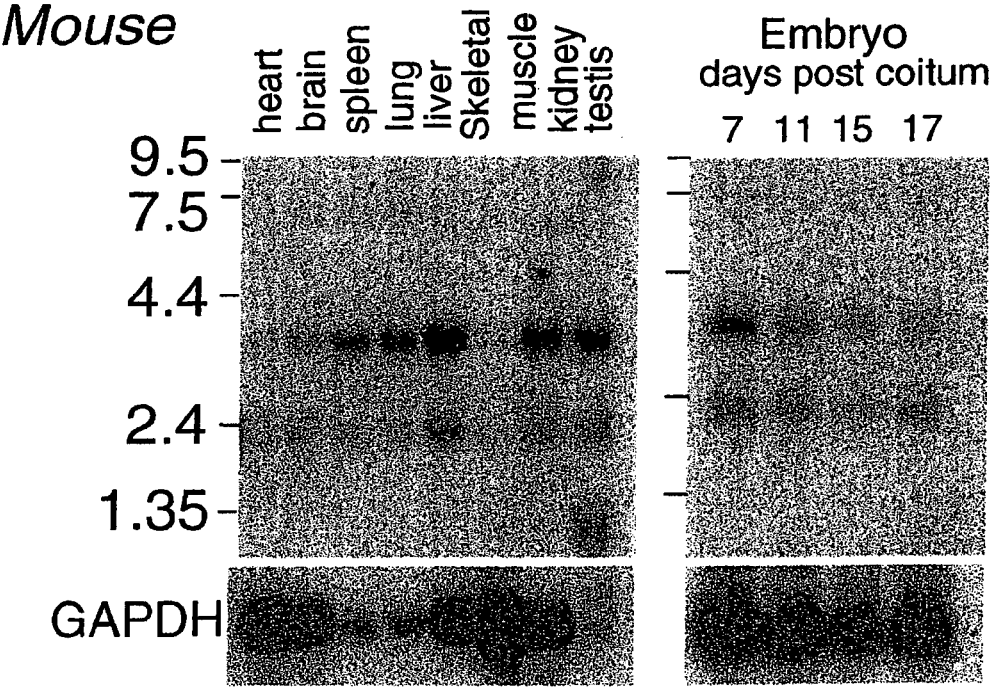

The TTRAP gene is widely expressed, as was already indicated by the presence of several partial TTRAP cDNA's in the EST sequence data base. The TTRAP expression was analyzed by Northern blot analysis against mRNA from different tissues, both from human and mouse (FIG. 2). Human TTRAP is present as a 2.2 kb transcript in all tissues tested. In addition to the 2.2 kb transcript, an additional 1.7 kb transcript is present in a testis sample (FIG. 2A).

Human TTRAP expression was further tested and found in the B-cell lines BJAB (Menezes et al., 1975) and DG75 (Ben-Bassat et al., 1977), in the Jurkat T-cell line and in HUVECs (Human umbilical vein endothelial cell).

For mouse TTRAP, two transcripts, one of 2.2 kb and one of 3.8 kb, were found on a murine multiple Northern blot (FIG. 2B). Mouse TTRAP mRNA was also detected in all tissues tested, be it to a lower extent in skeletal muscle. Both mouse transcripts are not only present in adult animals, but can also be detected in mouse embryo's from 7 to 17 days post coitus. These results are an indication that TTRAP plays an important role in early development.

On a multiple tissue Northern blot, a 4C4 probe recognizes 3 transcripts of 1.6 kb, 3.5 kb and 7.5 kb. All three mRNA's are present in spleen, thymus, prostate, testis, ovary, small intestine, colon and peripheral blood leukocytes. The expression of the 3.5 kb transcript is most prominent in testis. In ovary, the signal of the 7.5 kb mRNA is strongest.

Example 5

Co-immunoprecipitation of TTRAP with TNF-RII

It has been shown by two-hybrid analysis in yeast that TTRAP interacts with different receptors of the TNF-receptor superfamily, i.e., CD30, CD40 and TNF-RII (see, Table I). To confirm these results for one of these receptors in mammalian cells, co-immunoprecipitation of TTRAP with TNF-RII was carried out. In a typical experiment, 293T cells were transfected with HA-tagged TTRAP and TNF-RII (both in pCDNA expression vectors). TNF-RII was immunoprecipitated with the utr4 monoclonal antibody (gift from Roche, Basel). By Western blot on the immunoprecipitated fraction it was confirmed that TTRAP interacts with TNF-RII.

The method used hereto is as follows: A 9 cm dish with 293T Human Embryonic Kidney cells (approx. 30–50% confluent) is transfected with approximately 2 microgram of each expression plasmid. 24–48 hours after transfection, the cells are harvested and lysed in 300 microliter lysis buffer (50 mM Tris/HCl pH 7.4, 200 mM NaCl, 10% glycerol, 0.2% NP-40, 50 mM NaF, 1 mM $Na_3P_2O_7$, 1 mM $Na_3VO_4$ and protease inhibitors). The cell suspension is incubated for 20 minutes on ice. Cellular debris is pelleted for 10 minutes in an Eppendorf centrifuge, at 14.000 rpm and 4° C., and the supernatant is transferred into a fresh tube. 5 microgram antibody is added to the lysate, and incubated for 3 hours at 4° C., on a mixing platform. The samples are supplemented with 20 microliter of a 50% slurry of protein A or G beads and the incubation is continued for 1 hour. The beads are pelleted for 1 minute at minimal speed (approx. 500 rpm) and the supernatant is removed. The beads are resuspended in 750 microliter lysis buffer and immediately centrifuged again. This washing procedure is repeated, but this time samples are incubated for 10–15 minutes at 4° C. on a mixing platform. This is repeated twice more, to come to a total of 4 buffer changes. After the last wash, as much buffer as possible is to be removed, without sucking up Sepharose beads. After addition of 20 microliter sample buffer, the samples are stored at −20° C. or processed for SDS/PAGE.

10 microliters of each sample is analyzed to determine the protein CoIP and 3 microliters to verify the IP.

Interestingly, it was found that the association of TTRAP with the TNF receptor in an immunoprecipitation protocol from mammalian cells is preserved only if the immunoprecipitation procedure was performed in the presence of inhibitors of protein phosphatases, i.e., 50 mM NaF, 1 mM $Na_3P_2O_7$, 1 mM $Na_3VO_4$. This suggests that TTRAP and/or the receptor are phosphorylated, and that this phosphorylation is required for the interaction of both proteins.

Example 6

Interaction of TTRAP with TRAF3 and TRAF5

TTRAP was initially isolated in a two-hybrid screen in yeast, using the cytoplasmic domain of CD40 as bait. The interaction of TTRAP with CD40 could subsequently be confirmed by co-immunoprecipitation of both proteins, after over-expression in 293T human embryonic kidney cells. Because CD40 is known to associate with TRAFs in mammalian cells, it was investigated whether TTRAP could bind to TRAF3 and TRAF5.

The interaction of TTRAP with TRAF3 is disclosed in Table I. To investigate whether TTRAP could interact with TRAF5, a co-immunoprecipitation experiment was performed.

In this experiment, immunoprecipitation was carried out for Flag-tagged human TRAF5 (gift from Jun-ichiro Inoue, Dept Oncology, Inst. Med Sci., Univ. Tokyo, Japan) cells co-transfected with TRAF5 and TTRAP. Co-immunoprecipitation of HA-tagged TTRAP was detected by analyzing the immunoprecipitated proteins on Western blots. These results clearly demonstrate that TTRAP forms a complex with TRAF5 in mammalian cells.

Example 7

Interaction of TTRAP with CD40

To delineate the region in the cytoplasmic tail of CD40 that is important for TTRAP binding, deletion mutants of the receptor are made and are tested in co-immunoprecipitations and yeast two-hybrid assays. In a similar approach, deletion mutants of TTRAP are made to find out which region in the protein is necessary and sufficient for the interaction with CD40.

Example 8

Genomic TTRAP Sequence

Recently, the human genomic sequence for TTRAP has been deposited to the EMBL database (accession number HS30M3). The chromosome location of the genomic clone was mapped to 6p22.1–22.3. The TTRAP sequence within this clone was identified as a novel protein, termed dJ30M3.3 (acc number, CAA21141). The mRNA sequence starts at nucleotide 47,151 and ends at position 64,053. The protein encoding region starts at 47,168 and stops at 63,242, comprising 7 exons. The translational start and stop sites match those that were determined for TTRAP by cDNA library screening and the amino acid sequence is identical to the human sequence as disclosed herein.

The human TTRAP sequence also aligns with the *C. elegans* gene product Y63D3A.4 (accession number CEY63D3A_4). At the protein level, the sequences are approximately 30% identical. On the basis of the protein alignment it is assumed that this *C elegans* protein is the nematode homologue of human TTRAP.

Example 9

Identification of Novel CD40-interacting Proteins

A two-hybrid screening in yeast was performed with the cytoplasmic tail of human CD40 as a bait and a HeLa cDNA library as a prey. In this screening, the proteins encoded by the cDNAs listed below, were picked up as a result of their interaction with CD40.

1. A partial cDNA encoding human Bloom's syndrome protein (BLM) (accession number U39817). The complete cDNA sequence of BLM is 4,437 nucleotides. The protein encoding sequence starts at nucleotide 75 and stops at nucleotide 4,328. The size of the protein is 1,418 amino acids. The partial cDNA that was picked up in the two-hybrid screen with CD40 starts at nucleotide 529, which corresponds to amino acid 151. The 3'-end of this partial cDNA clone has not been determined yet.
2. A partial cDNA encoding for human nuclear autoantigen (SP-100) (accession number M60618). The complete cDNA sequence of SP-100 is 1,879 nucleotides. The protein encoding sequence starts at nucleotide 32 and stops at nucleotide 1,474. The size of the protein is 481 amino acids. The partial cDNA that was picked up in the two-hybrid screen with CD40 starts at nucleotide 699, which corresponds to amino acid 223, and reaches till the end of the SP-100 cDNA sequence.
3. A partial cDNA sequence for the human homologue of the mouse BP75 protein (accession number AF084259). The complete cDNA sequence of the mouse protein BP75 is 2,361 nucleotides. The protein encoding sequence starts at nucleotide 211 and stops at nucleotide 2,166. The size of the protein is 652 amino acids. The partial cDNA that was picked up in the two-hybrid screen with CD40 aligns with the mouse cDNA sequence starting at nucleotide 1,070, which corresponds to amino acid 286, and goes to the end of the BP75 cDNA sequence. The mouse and the human cDNA sequences are 83% identical. The human genomic sequence of BP75 has also been deposited to the database (accession number Z99496). The cDNA of mouse BP75 is approximately 83% identical to the human genomic PAC clone (from nucleotide 122564-120820). The chromosome location of the human PAC clone was mapped to 6q22.1–22.33.

Example 10

Isolation of DAXX as a CD40-interacting Protein by Yeast Two-hybrid

In a yeast two-hybrid assay with the cytoplasmic tail of human CD40 as a bait, a partial cDNA was picked up encoding the human Fas-binding protein (DAXX) (accession number AF039136). The complete cDNA sequence of DAXX is 2,487 nucleotides. The protein encoding sequence starts at nucleotide 148 and stops at nucleotide 2,370. The size of the protein is 741 amino acids. The partial cDNA that was picked up in the two-hybrid screen with CD40 starts at nucleotide 1,500, which corresponds to amino acid 451, and goes to the end of the DAXX cDNA sequence.

Fas and CD40 are both members of the TNF-Receptor superfamily. DAXX was originally isolated as a Fas-binding protein in a yeast two-hybrid screen (Yang et al., Cell, 89, 1067–76, 1997). The protein was shown to interact specifically with the death domain of Fas. It was reported to play a role in apoptosis via the activation of the Jun N-terminal kinase. The authors examined the binding of a partial clone of human DAXX (from amino acid 501 till the end) to the cytoplasmic tail of mouse CD40 and could not detect interaction. In addition, an in vitro interaction assay of full length DAXX with glutothione S-tranferase-CD40 ("GST-CD40") also turned out to be negative. Therefore, the authors conclude that DAXX does not associate with CD40.

The discrepancy between some of the findings reported in Yang et al. and the observation according to the current invention that the cytoplasmic tail of CD40 does interact with DAXX in yeast two-hybrid could be due to the following reasons: i) In the two-hybrid interaction assay that was performed, Yang et al. use a shorter partial clone of DAXX than the one picked up according to the present invention. In addition, interaction of a partial human DAXX with human CD40 is observed in the underlying invention, whereas Yang et al., use a partial human DAXX and mouse CD40; and ii) The in vitro binding assay that Yang et al. use may not be sensitive enough to detect the interaction of full-length DAXX and CD40 protein. Moreover, it is unclear whether in this assay Yang et al. use both proteins from the same species.

REFERENCES

Banchereau, J; Bazan, F.; Blanchard, D.; Briere, F.; Galizzi, J. P.; Van Kooten, C.; Liu, Y. J.; Rousset, F.; Saeland, S. (1994). The CD40 antigen and its ligand. *Annu. Rev. Immunol.* 12, 881.

Ben-Bassat, H.; Goldblum, N.; Mitrani, S.; Goldblum, T.; Yoffey, J. M.; Cohen, M. M.; Bentwich, Z.; Ramot, B.; Klein, E.; Klein, G. (1977). Establishment in continuous culture of a new type of lymphocyte from a "Burkitt like" malignant lymphoma (line D.G.-75). *Int. J. Cancer* 19, 27.

Chaudhuri, A.; Orme, S.; Eilan, S.; Cheranyl, B. J. (1997). CD40 mediated signals inhibit the binding of TNF receptor associated factor 2 to the CD40 cytoplasmic domain. *J. Immunol.* 159, 4244.

Durie, F. H.; Fava, R. A.; Foy, T. M., Aruffo, A.; Ledbetter, J. A.; Noelle, R. J. (1993). Prevention of collagen-induced arthritis with an antibody to gp39, the ligand for CD40. *Science* 261, 1328.

Francis, D. A.; Karras, J. G.; Ke, X. Y.; Sen R.; Rothstein, T. L. (1995). Induction of the transcription factors NF-kappa B, AP-1 and NF-AT during B cell stimulation through the CD40 receptor. *Int. Immunol.* 7, 151.

Fries, K. M.; Sempowski, G. D.; Gaspari, A. A.; Blieden, R. J.; Looney, R. J.; Philips, R. P. (1995). CD40 expression by human fibroblasts. *Clin. Immunol. Immunopath.* 77, 42.

Galy, A.; Spits, H. (1992). CD40 is functionally expressed on human thymic epithelial cells. *J. Immunol.* 149, 775.

Gaspari, A. A.; Sempowski, G. D.; Chess, P.; Gish, J.; Phillips, R. P. (1996). Human epidermal keratinocytes are induced to secrete interleukin-6 and costimulate T lymphocyte proliferation by a CD40-dependent mechanism. *Eur. J. Immunol.* 26, 1371.

Gerritse, K.; Laman, J. D.; Noelle, R. J.; Arufo, A.; Ledbetter, J. A.; Boersma, W. J. A.; Claassen, E. (1996). CD40–CD40 ligand interactions in experimental allergic encephalomyelitis and multiple sclerosis. *Proc. Natl. Acad. Sci. USA* 93, 2499.

Gietz, R. D.; Schiestl, R. H.; Willems, A. R.; Woods, R. A. (1995). Studies on the transformation of intact yeast, cells by the LiAc/SS-DNA/PEG procedure. *Yeast*, 11, 355.

Green, C. B.; Beshare, J. C. (1996). Identification of a novel vertebrate circadian clock-regulated gene encoding the protein nocturnin. *Proc. Natl. Acad. Sci. USA* 93, 14884.

Griggs, N.; Agersborg, S.; Noelle, R. J.; Ledbetter, J.; Linsley, P.; Tung, K. (1996). The relative contribution of the CD28 and gp39 costimulatory pathways in the clonal expansion and pathogenic acquisition of self-reactive T cells. *J. Exp. Med.* 180, 801.

Gyuris, J.; Golemis, E.; Chertkov, H.; Brent, R. (1993). Cdi1, a human G1 and S phase protein phosphatase that associates with Cdk2. *Cell* 75, 791.

Hollenbaugh, D.; Mischel-Petty, N.; Edwards, C. P.; Simon, J. C.; Denfeld, R. W.; Kienerm, P. A.; Aruffo, A. (1995). Expression of functional CD40 by vascular endothelial cells. *J. Exp. Med.* 182, 33.

Ishida, T.; Tojo, T.; Aoli, T.; Kobayashi, N.; Ohishi, T.; Watanabe, T.; Yamamoto, T.; Inoue, J. (1996). TRAF5, a novel tumor necrosis factor receptor associated factor family protein, mediated CD40 signalling. *Proc. Natl. Acad. Sci. USA* 93, 9437.

Karmann, K.; Min, W.; Fanslow, W. C.; Prober, J. S. (1996). Activation and homologous desentization of human endothelial cells by CD40 ligand, tumor necrosis factor and interleukin 1. *J. Exp. Med.* 184, 173.

Kashiwada, M.; Shirakata, Y.; Inoue, J-I.; Nakano, H.; Okazaki, K.; Okumura, K.;, Yamamoto, T.; Nagaoka, H.; Takemori, T. (1998). Tumor Necrosis Factor Receptor-associated Factor 6 (TRAF6) stimulates extracellular signal-regulated kinase (ERK) activity in CD40 signalling along a Ras-independent pathway. *J. Exp. Med.* 187, 237.

Malvar, T.; Biron, R. W.; Kaback, D. B.; Denis, C. L. (1992). The CCR4 protein from *Saccharomyces cerevisiae* contains a leucine rich repeat region which is required for its control of ADH2 gene expression. *Genetics*, 132, 951.

Menezes, J.; Leibold, W.; Klein, G.; Clements, G. (1975). Establishment and characterization of an Epstein-Barr virus (EBC)-negative lymphoblastoid B cell line (BJA-B) from an exceptional, EBV-genome-negative African Burkitt's lymphoma. *Biomedicine* 22, 276.

Noelle, R. J. (1996). CD40 and its ligand in host defense. *Immunity*, 4, 415–419.

Puech, A.; Dupressoir, A.; Loireau, M.; Mattei, M.; Heidemann, T. (1997). Characterization of two age-induced intracisternal A-particle-related transcripts in the mouse liver. *J. Biol. Chem.* 272, 5995.

Stamenkovic, I.; Clark, E. A.; Seed, B. (1989). A B-lymphocyte activation molecule related to the nerve growth factor receptor and induced by cytokines in carcinomas. *Embo J.* 8, 1403.

What is claimed is:

1. An isolated nucleic acid sequence encoding a protein, said protein characterized by an ability to form a complex with receptors of the Tumor Necrosis Factor ("TNF") superfamily including the cytoplasmic domain of CD40 as determined by a yeast two-hybrid interaction assay or a co-immunoprecipitation assay, said protein comprising amino acids 54–140 of SEQ ID NO:2, or amino acids 54–362 of SEQ ID NO:2, or amino acids 54–273 of SEQ ID NO:2, or amino acids 54–236 of SEQ ID NO:2.

2. The isolated nucleic acid sequence of claim 1 comprising the nucleotide sequence encoding SEQ ID NO:2.

3. An isolated nucleic acid sequence encoding a protein comprising SEQ ID NO:6 or a fragment thereof comprising amino acids 2–245 of SEQ ID NO:6.

* * * * *

UNITED STATES PATENT AND TRADEMARK OFFICE
CERTIFICATE OF CORRECTION

| | |
|---|---|
| PATENT NO. | : 7,098,322 B2 |
| APPLICATION NO. | : 10/757745 |
| DATED | : August 29, 2006 |
| INVENTOR(S) | : Stefan M. C. Pype, Jacques E. F. Remacle and Danny F. E. Huylebroeck |

It is certified that error appears in the above-identified patent and that said Letters Patent is hereby corrected as shown below:

In the specification:
COLUMN 4, LINE 15, change "maybe" to --may be--
COLUMN 16, LINE 1, change "ofthe" to --of the--
COLUMN 18, LINE 11, delete the comma after "yeast"

Signed and Sealed this

Sixteenth Day of December, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 1920
<212> TYPE: DNA
<213> ORGANISM: Homo sapiens
<220> FEATURE:
<221> NAME/KEY: misc_feature
<222> LOCATION: (1627)..(1627)
<223> OTHER INFORMATION: N stands for any nucleotide.
<220> FEATURE:
<221> NAME/KEY: CDS
<222> LOCATION: (20)..(1108)
<223> OTHER INFORMATION:
<220> FEATURE:
<221> NAME/KEY: misc_feature
<222> LOCATION: (1849)..(1849)
<223> OTHER INFORMATION: N stands for any nucleotide.

<400> SEQUENCE: 1

```
gtgcagaggc ggcaggaag atg gag ttg ggg agt tgc ctg gag ggc ggg agg        52
                    Met Glu Leu Gly Ser Cys Leu Glu Gly Gly Arg
                     1               5                  10 gag gcg gcg gag gaa gag ggc gag cct gag gtg aaa aag cgg cga ctt        100
Glu Ala Ala Glu Glu Glu Gly Glu Pro Glu Val Lys Lys Arg Arg Leu
            15                  20                  25 ctg tgt gtg gag ttt gcc tcg gtc gca agc tgc gat gcc gca gtg gct        148
Leu Cys Val Glu Phe Ala Ser Val Ala Ser Cys Asp Ala Ala Val Ala
        30                  35                  40 cag tgc ttc ctg gcc gag aac gac tgg gag atg gaa agg gct ctg aac        196
Gln Cys Phe Leu Ala Glu Asn Asp Trp Glu Met Glu Arg Ala Leu Asn
    45                  50                  55 tcc tac ttc gag cct ccg gtg gag gag agc gcc ttg gaa cgc cga cct        244
Ser Tyr Phe Glu Pro Pro Val Glu Glu Ser Ala Leu Glu Arg Arg Pro
60                  65                  70                  75 gaa acc atc tct gag ccc aag acc tat gtt gac cta acc aat gaa gaa        292
Glu Thr Ile Ser Glu Pro Lys Thr Tyr Val Asp Leu Thr Asn Glu Glu
                80                  85                  90 aca act gat tcc acc act tct aaa atc agc cca tct gaa gat act cag        340
Thr Thr Asp Ser Thr Thr Ser Lys Ile Ser Pro Ser Glu Asp Thr Gln
            95                 100                 105 caa gaa aat ggc agc atg ttc tct ctc att acc tgg aat att gat gga        388
Gln Glu Asn Gly Ser Met Phe Ser Leu Ile Thr Trp Asn Ile Asp Gly
        110                 115                 120 tta gat cta aac aat ctg tca gag agg gct cga ggg gtg tgt tcc tac        436
Leu Asp Leu Asn Asn Leu Ser Glu Arg Ala Arg Gly Val Cys Ser Tyr
    125                 130                 135 tta gct ttg tac agc cca gat gtg ata ttt cta cag gaa gtt att ccc        484
Leu Ala Leu Tyr Ser Pro Asp Val Ile Phe Leu Gln Glu Val Ile Pro
140                 145                 150                 155 cca tat tat agc tac cta aag aag aga tca agt aat tat gag att att        532
Pro Tyr Tyr Ser Tyr Leu Lys Lys Arg Ser Ser Asn Tyr Glu Ile Ile
                160                 165                 170 aca ggt cat gaa gaa gga tat ttc aca gct ata atg ttg aag aaa tca        580
Thr Gly His Glu Glu Gly Tyr Phe Thr Ala Ile Met Leu Lys Lys Ser
            175                 180                 185 aga gtg aaa tta aaa agc caa gag att att cct ttt cca agt acc aaa        628
Arg Val Lys Leu Lys Ser Gln Glu Ile Ile Pro Phe Pro Ser Thr Lys
        190                 195                 200 atg atg aga aac ctt tta tgt gtg cat gtg aat gtg tca gga aat gag        676
Met Met Arg Asn Leu Leu Cys Val His Val Asn Val Ser Gly Asn Glu
    205                 210                 215
```

| | | |
|---|---|---|
| ctt tgc ctt atg aca tcc cat ttg gag agc acc aga ggg cat gct gcg<br>Leu Cys Leu Met Thr Ser His Leu Glu Ser Thr Arg Gly His Ala Ala<br>220                        225                    230                  235 | | 724 |
| gaa cga atg aat cag tta aaa atg gtt tta aag aaa atg caa gag gct<br>Glu Arg Met Asn Gln Leu Lys Met Val Leu Lys Lys Met Gln Glu Ala<br>                    240                    245                    250 | | 772 |
| cca gag tca gct aca gtt ata ttt gca gga gat aca aat cta agg gat<br>Pro Glu Ser Ala Thr Val Ile Phe Ala Gly Asp Thr Asn Leu Arg Asp<br>255                        260                    265 | | 820 |
| cga gag gtt acc aga tgt ggt ggt tta ccc aac aac att gtg gat gtc<br>Arg Glu Val Thr Arg Cys Gly Gly Leu Pro Asn Asn Ile Val Asp Val<br>                    270                    275                    280 | | 868 |
| tgg gag ttt ttg ggc aaa cct aaa cat tgc cag tat aca tgg gat aca<br>Trp Glu Phe Leu Gly Lys Pro Lys His Cys Gln Tyr Thr Trp Asp Thr<br>285                        290                    295 | | 916 |
| caa atg aac tct aat ctt gga ata act gct gct tgt aaa ctt cgt ttt<br>Gln Met Asn Ser Asn Leu Gly Ile Thr Ala Ala Cys Lys Leu Arg Phe<br>300                        305                    310                    315 | | 964 |
| gat cga ata ttt ttc aga gca gca gca gaa gag gga cac att att ccc<br>Asp Arg Ile Phe Phe Arg Ala Ala Ala Glu Glu Gly His Ile Ile Pro<br>                    320                    325                    330 | | 1012 |
| cga agt ttg gac ctt ctt gga tta gaa aaa ctg gac tgt ggt aga ttt<br>Arg Ser Leu Asp Leu Leu Gly Leu Glu Lys Leu Asp Cys Gly Arg Phe<br>335                        340                    345 | | 1060 |
| cct agt gat cac tgg ggt ctt ctg tgc aac tta gat ata ata ttg taa<br>Pro Ser Asp His Trp Gly Leu Leu Cys Asn Leu Asp Ile Ile Leu<br>                    350                    355                    360 | | 1108 |
| aatgcttttc aagtgtgggt tttgccctga ttgttgcaaa tacaatttcc accttctgga | | 1168 |
| aaggtaggtt tgctgtggag gaaataatgt actagatcat tgtcacagaa aaaccaacta | | 1228 |
| tgatttatgg ttgtgttttc agaattcaac attaaagatt aatgtttatt taaacgaaca | | 1288 |
| cattcctgca ttcaggatgt gaggccattt aataaaaagg gcacaaagcc tgtcagagtt | | 1348 |
| ttcaacggtg cttacagctg ccagctggat tccaaacagg taccccattg tctctgagct | | 1408 |
| aatgttttata tttttccatt caggcaccga aatagttaat atttaaaata agtcttcaaa | | 1468 |
| agaaaacata agagattatt gagttcttgg gactggatcc tttatttcat aagttcagat | | 1528 |
| catcttaaat gaaaatgcca tgattatctg cagttaagta gatgacagct attctacatc | | 1588 |
| agacttgatt tttgtcagct aattacataa ttggtaagnt ataattgaaa ccttatggct | | 1648 |
| taaaattcct taactccttt ttgattcatg tttgtagtca tgttgtcaac agaggcaaag | | 1708 |
| ttaagcttga tgatggttaa aatcggtttg atagcaccat gggacatttt tttaacaaaa | | 1768 |
| ataaatgcat gaagagacat agccttttag ttttgctaat tgtgaaatgg aaatgcttta | | 1828 |
| caggaagtaa atgcaaatta nttttaagtg tgctttaaag aaaaatattt tccccacagg | | 1888 |
| agaaatttaa ataagaatt ttatttggta aa | | 1920 |

<210> SEQ ID NO 2
<211> LENGTH: 362
<212> TYPE: PRT
<213> ORGANISM: Homo sapiens

<400> SEQUENCE: 2

Met Glu Leu Gly Ser Cys Leu Glu Gly Gly Arg Glu Ala Ala Glu Glu
1                 5                     10                   15

Glu Gly Glu Pro Glu Val Lys Lys Arg Arg Leu Leu Cys Val Glu Phe
                   20                     25                   30

```
Ala Ser Val Ala Ser Cys Asp Ala Ala Val Ala Gln Cys Phe Leu Ala
        35                  40                  45
Glu Asn Asp Trp Glu Met Glu Arg Ala Leu Asn Ser Tyr Phe Glu Pro
    50                  55                  60
Pro Val Glu Glu Ser Ala Leu Glu Arg Arg Pro Glu Thr Ile Ser Glu
65                  70                  75                  80
Pro Lys Thr Tyr Val Asp Leu Thr Asn Glu Glu Thr Thr Asp Ser Thr
                85                  90                  95
Thr Ser Lys Ile Ser Pro Ser Glu Asp Thr Gln Gln Glu Asn Gly Ser
            100                 105                 110
Met Phe Ser Leu Ile Thr Trp Asn Ile Asp Gly Leu Asp Leu Asn Asn
        115                 120                 125
Leu Ser Glu Arg Ala Arg Gly Val Cys Ser Tyr Leu Ala Leu Tyr Ser
    130                 135                 140
Pro Asp Val Ile Phe Leu Gln Glu Val Ile Pro Pro Tyr Tyr Ser Tyr
145                 150                 155                 160
Leu Lys Lys Arg Ser Ser Asn Tyr Glu Ile Ile Thr Gly His Glu Glu
                165                 170                 175
Gly Tyr Phe Thr Ala Ile Met Leu Lys Lys Ser Arg Val Lys Leu Lys
            180                 185                 190
Ser Gln Glu Ile Ile Pro Phe Pro Ser Thr Lys Met Met Arg Asn Leu
        195                 200                 205
Leu Cys Val His Val Asn Val Ser Gly Asn Glu Leu Cys Leu Met Thr
    210                 215                 220
Ser His Leu Glu Ser Thr Arg Gly His Ala Ala Glu Arg Met Asn Gln
225                 230                 235                 240
Leu Lys Met Val Leu Lys Lys Met Gln Glu Ala Pro Glu Ser Ala Thr
                245                 250                 255
Val Ile Phe Ala Gly Asp Thr Asn Leu Arg Asp Arg Glu Val Thr Arg
            260                 265                 270
Cys Gly Gly Leu Pro Asn Asn Ile Val Asp Val Trp Glu Phe Leu Gly
        275                 280                 285
Lys Pro Lys His Cys Gln Tyr Thr Trp Asp Thr Gln Met Asn Ser Asn
    290                 295                 300
Leu Gly Ile Thr Ala Ala Cys Lys Leu Arg Phe Asp Arg Ile Phe Phe
305                 310                 315                 320
Arg Ala Ala Glu Glu Gly His Ile Ile Pro Arg Ser Leu Asp Leu
                325                 330                 335
Leu Gly Leu Glu Lys Leu Asp Cys Gly Arg Phe Pro Ser Asp His Trp
            340                 345                 350
Gly Leu Leu Cys Asn Leu Asp Ile Ile Leu
        355                 360

<210> SEQ ID NO 3
<211> LENGTH: 1312
<212> TYPE: DNA
<213> ORGANISM: Mus musculus
<220> FEATURE:
<221> NAME/KEY: CDS
<222> LOCATION: (122)..(1234)
<223> OTHER INFORMATION:

<400> SEQUENCE: 3
agctattaat gattcgaatt tatacgactc actataggga atttggccct cgaggccaag      60
aattcggcac gagggcggga agcagcgtga agagcgggtg ttttgagggg accctgcggc    120
```

-continued

```
g atg gcg tct ggc agc agt tcc gat gcg gcg gag ccc gca ggg ccg gca          169
  Met Ala Ser Gly Ser Ser Asp Ala Ala Glu Pro Ala Gly Pro Ala
  1               5                   10                  15 ggg cgg gcg gcg tcg gcg ccc gaa gca gca cag gcg gag gag gac cgg            217
Gly Arg Ala Ala Ser Ala Pro Glu Ala Ala Gln Ala Glu Glu Asp Arg
            20                  25                  30 gtg aag agg cgg cgg ctt cag tgc ctg ggc ttt gcg ttg gtg ggg gga            265
Val Lys Arg Arg Arg Leu Gln Cys Leu Gly Phe Ala Leu Val Gly Gly
        35                  40                  45 tgc gac ccc acg atg gtc ccc agc gtc ctg cgg gag aac gac tgg cag            313
Cys Asp Pro Thr Met Val Pro Ser Val Leu Arg Glu Asn Asp Trp Gln
50                  55                  60 acg cag aaa gcc ctg agc gcc tac ttc gag ctg cca gag aac gac caa            361
Thr Gln Lys Ala Leu Ser Ala Tyr Phe Glu Leu Pro Glu Asn Asp Gln
65              70                  75                  80 ggg tgg ccg cgc cag cct ccc acg tcc ttc aag tcc gag gcc tat gtt            409
Gly Trp Pro Arg Gln Pro Pro Thr Ser Phe Lys Ser Glu Ala Tyr Val
                85                  90                  95 gat cta acc aac gag gat gca aat gat aca acc att tta gaa gcc agt            457
Asp Leu Thr Asn Glu Asp Ala Asn Asp Thr Thr Ile Leu Glu Ala Ser
            100                 105                 110 cca tct gga act cct cta gaa gat agc agc act att tct ttc att acc            505
Pro Ser Gly Thr Pro Leu Glu Asp Ser Ser Thr Ile Ser Phe Ile Thr
        115                 120                 125 tgg aat att gat gga tta gat gga tgc aat ctg ccc gag agg gct cga            553
Trp Asn Ile Asp Gly Leu Asp Gly Cys Asn Leu Pro Glu Arg Ala Arg
    130                 135                 140 ggg gtg tgt tcc tgc cta gct ttg tat agt cca gat gtg gta ttt cta            601
Gly Val Cys Ser Cys Leu Ala Leu Tyr Ser Pro Asp Val Val Phe Leu
145                 150                 155                 160 cag gaa gtt atc ccc cca tac tgt gcc tac cta aag aag aga gca gcc            649
Gln Glu Val Ile Pro Pro Tyr Cys Ala Tyr Leu Lys Lys Arg Ala Ala
                165                 170                 175 agt tac aca att att aca ggt aat gaa gaa gga tat ttc aca gct ata            697
Ser Tyr Thr Ile Ile Thr Gly Asn Glu Glu Gly Tyr Phe Thr Ala Ile
            180                 185                 190 cta ttg aag aaa gga aga gtg aaa ttt aaa agt cag gag att att cct            745
Leu Leu Lys Lys Gly Arg Val Lys Phe Lys Ser Gln Glu Ile Ile Pro
        195                 200                 205 ttt cca aat acc aaa atg atg aga aac ctg cta tgc gta aat gtg agt            793
Phe Pro Asn Thr Lys Met Met Arg Asn Leu Leu Cys Val Asn Val Ser
    210                 215                 220 ttg ggt gga aat gaa ttt tgc ctt atg aca tcc cat ttg gag agc acc            841
Leu Gly Gly Asn Glu Phe Cys Leu Met Thr Ser His Leu Glu Ser Thr
225                 230                 235                 240 aga gaa cat tct gcg gaa cga ata aga caa tta aaa act gtt ctt gga            889
Arg Glu His Ser Ala Glu Arg Ile Arg Gln Leu Lys Thr Val Leu Gly
                245                 250                 255 aaa atg caa gag gct cca gat tca acc acg gtt ata ttt gca gga gat            937
Lys Met Gln Glu Ala Pro Asp Ser Thr Thr Val Ile Phe Ala Gly Asp
            260                 265                 270 aca aat tta aga gat caa gaa gtt atc aaa tgt ggt ggt tta cct gac            985
Thr Asn Leu Arg Asp Gln Glu Val Ile Lys Cys Gly Gly Leu Pro Asp
        275                 280                 285 aac gtt ttt gat gcc tgg gaa ttt tta ggc aaa cct aaa cat tgc cag            1033
Asn Val Phe Asp Ala Trp Glu Phe Leu Gly Lys Pro Lys His Cys Gln
    290                 295                 300 tat aca tgg gat acg aaa gca aat aac aac ctc agg atc cct gct gct            1081
Tyr Thr Trp Asp Thr Lys Ala Asn Asn Asn Leu Arg Ile Pro Ala Ala
305                 310                 315                 320
```

-continued

```
tat aag cat cgt ttt gat cga ata ttt ttc aga gca gaa gag ggg cac      1129
Tyr Lys His Arg Phe Asp Arg Ile Phe Phe Arg Ala Glu Glu Gly His
            325                 330                 335 ctt att cct caa agt tta gac ctt gtt ggg ttg gaa aaa ctg gac tgt      1177
Leu Ile Pro Gln Ser Leu Asp Leu Val Gly Leu Glu Lys Leu Asp Cys
            340                 345                 350 ggt aga ttt ccg agt gat cac tgg ggg ctc ttg tgc acc ttg aat gta      1225
Gly Arg Phe Pro Ser Asp His Trp Gly Leu Leu Cys Thr Leu Asn Val
            355                 360                 365 gta ttg tga aaagcttccc acttgcagct ttacacgttt gttagcacta              1274
Val Leu
    370 gttctgaatt tgtgtaggtc tcaacctttc aggacatc                            1312

<210> SEQ ID NO 4
<211> LENGTH: 370
<212> TYPE: PRT
<213> ORGANISM: Mus musculus

<400> SEQUENCE: 4

Met Ala Ser Gly Ser Ser Ser Asp Ala Ala Glu Pro Ala Gly Pro Ala
1               5                   10                  15

Gly Arg Ala Ala Ser Ala Pro Glu Ala Ala Gln Ala Glu Glu Asp Arg
            20                  25                  30

Val Lys Arg Arg Arg Leu Gln Cys Leu Gly Phe Ala Leu Val Gly Gly
        35                  40                  45

Cys Asp Pro Thr Met Val Pro Ser Val Leu Arg Glu Asn Asp Trp Gln
    50                  55                  60

Thr Gln Lys Ala Leu Ser Ala Tyr Phe Glu Leu Pro Glu Asn Asp Gln
65                  70                  75                  80

Gly Trp Pro Arg Gln Pro Pro Thr Ser Phe Lys Ser Glu Ala Tyr Val
                85                  90                  95

Asp Leu Thr Asn Glu Asp Ala Asn Asp Thr Thr Ile Leu Glu Ala Ser
            100                 105                 110

Pro Ser Gly Thr Pro Leu Glu Asp Ser Ser Thr Ile Ser Phe Ile Thr
        115                 120                 125

Trp Asn Ile Asp Gly Leu Asp Gly Cys Asn Leu Pro Glu Arg Ala Arg
    130                 135                 140

Gly Val Cys Ser Cys Leu Ala Leu Tyr Ser Pro Asp Val Val Phe Leu
145                 150                 155                 160

Gln Glu Val Ile Pro Pro Tyr Cys Ala Tyr Leu Lys Lys Arg Ala Ala
                165                 170                 175

Ser Tyr Thr Ile Ile Thr Gly Asn Glu Glu Gly Tyr Phe Thr Ala Ile
            180                 185                 190

Leu Leu Lys Lys Gly Arg Val Lys Phe Lys Ser Gln Glu Ile Ile Pro
        195                 200                 205

Phe Pro Asn Thr Lys Met Met Arg Asn Leu Leu Cys Val Asn Val Ser
    210                 215                 220

Leu Gly Gly Asn Glu Phe Cys Leu Met Thr Ser His Leu Glu Ser Thr
225                 230                 235                 240

Arg Glu His Ser Ala Glu Arg Ile Arg Gln Leu Lys Thr Val Leu Gly
                245                 250                 255

Lys Met Gln Glu Ala Pro Asp Ser Thr Thr Val Ile Phe Ala Gly Asp
            260                 265                 270

Thr Asn Leu Arg Asp Gln Glu Val Ile Lys Cys Gly Gly Leu Pro Asp
```

-continued

```
                 275                 280                 285
Asn Val Phe Asp Ala Trp Glu Phe Leu Gly Lys Pro Lys His Cys Gln
    290                 295                 300

Tyr Thr Trp Asp Thr Lys Ala Asn Asn Asn Leu Arg Ile Pro Ala Ala
305                 310                 315                 320

Tyr Lys His Arg Phe Asp Arg Ile Phe Phe Arg Ala Glu Gly His
                325                 330                 335

Leu Ile Pro Gln Ser Leu Asp Leu Val Gly Leu Glu Lys Leu Asp Cys
                340                 345                 350

Gly Arg Phe Pro Ser Asp His Trp Gly Leu Leu Cys Thr Leu Asn Val
                355                 360                 365

Val Leu
    370

<210> SEQ ID NO 5
<211> LENGTH: 1536
<212> TYPE: DNA
<213> ORGANISM: Homo sapiens
<220> FEATURE:
<221> NAME/KEY: misc_feature
<222> LOCATION: (1530)..(1531)
<223> OTHER INFORMATION: N stands for any nucleotide.
<220> FEATURE:
<221> NAME/KEY: CDS
<222> LOCATION: (209)..(1534)
<223> OTHER INFORMATION:
<220> FEATURE:
<221> NAME/KEY: misc_feature
<222> LOCATION: (1392)..(1392)
<223> OTHER INFORMATION: N stands for any nucleotide.

<400> SEQUENCE: 5
agagaaagag gctccgggga gatagcggac cagtgagggc tgcccctctt ttgaagcggt     60
tttcgtctct ttccgccagt ggcctccag ctcacgcagg ggcgggtccc ggtagcgcga    120
ggcggtgcag ggcgggaagg ggagtggtgg cggctgcggc agtagggaca gcaggagcag    180
tggtgctgtc agcgcggccg tcggagac atg gga gac ccg ggg tcg gaa ata      232
                                Met Gly Asp Pro Gly Ser Glu Ile
                                  1               5 ata gaa tct gtc cct cca gct ggc cct gag gca tct gag tca aca acg     280
Ile Glu Ser Val Pro Pro Ala Gly Pro Glu Ala Ser Glu Ser Thr Thr
     10                  15                  20 gat gaa aat gaa gac gac att cag ttt gtc agt gaa gga cca tcg aga     328
Asp Glu Asn Glu Asp Asp Ile Gln Phe Val Ser Glu Gly Pro Ser Arg
25                  30                  35                  40 cct gtt ctt gaa tac atc gat ctg gtc tgt ggt gat gat gaa aac cct     376
Pro Val Leu Glu Tyr Ile Asp Leu Val Cys Gly Asp Asp Glu Asn Pro
                 45                  50                  55 agc gcc tat tat agt gat att ctg ttt cct aaa atg cca aaa cga cag     424
Ser Ala Tyr Tyr Ser Asp Ile Leu Phe Pro Lys Met Pro Lys Arg Gln
             60                  65                  70 ggt gat ttt ttg cat ttt tta aat atg aag aag gtg aaa aca gac aca     472
Gly Asp Phe Leu His Phe Leu Asn Met Lys Lys Val Lys Thr Asp Thr
         75                  80                  85 gaa aat aat gaa gtg agc aaa aat cac tgc aga ttg tct aag gca aag     520
Glu Asn Asn Glu Val Ser Lys Asn His Cys Arg Leu Ser Lys Ala Lys
     90                  95                 100 gaa cca cat ttc gag tat ata gaa caa cca atc att gaa gaa aag cca     568
Glu Pro His Phe Glu Tyr Ile Glu Gln Pro Ile Ile Glu Glu Lys Pro
105                 110                 115                 120 tca ctt tca tca aag aaa gaa ata gat aat ctt gtg ctt cca gat tgt     616
```

```
                Ser Leu Ser Ser Lys Lys Glu Ile Asp Asn Leu Val Leu Pro Asp Cys
                            125                 130                 135 tgg aat gaa aaa caa gca ttt atg ttt aca gaa caa tac aaa tgg ctt              664
Trp Asn Glu Lys Gln Ala Phe Met Phe Thr Glu Gln Tyr Lys Trp Leu
            140                 145                 150 gaa ata aaa gaa ggt aaa tta gga tgt aag gat tgt tca gca gtt cgg              712
Glu Ile Lys Glu Gly Lys Leu Gly Cys Lys Asp Cys Ser Ala Val Arg
            155                 160                 165 cat ttg gga tcg aaa gca gaa aag cat gtc cat gtg tcc aag gaa tgg              760
His Leu Gly Ser Lys Ala Glu Lys His Val His Val Ser Lys Glu Trp
        170                 175                 180 att gca tat tta gta acc cct aat ggc agt aat aaa act act agg caa              808
Ile Ala Tyr Leu Val Thr Pro Asn Gly Ser Asn Lys Thr Thr Arg Gln
185                 190                 195                 200 gct tct cta cga aaa aaa att agg gaa cat gat gtt tct aaa gcc cat              856
Ala Ser Leu Arg Lys Lys Ile Arg Glu His Asp Val Ser Lys Ala His
                205                 210                 215 ggt aaa att cag gat ttg tta aag gaa tca act aat gat tca att tgt              904
Gly Lys Ile Gln Asp Leu Leu Lys Glu Ser Thr Asn Asp Ser Ile Cys
            220                 225                 230 aat tta gtg cat aaa caa aat aat aaa aat att gat gct act gta aaa              952
Asn Leu Val His Lys Gln Asn Asn Lys Asn Ile Asp Ala Thr Val Lys
            235                 240                 245 gtt ttc aat act gtt tac agt tta gta aaa cat aac aga cct tta tct             1000
Val Phe Asn Thr Val Tyr Ser Leu Val Lys His Asn Arg Pro Leu Ser
250                 255                 260 gat att gag ggg gca aga gaa tta cag gaa aaa aat gga gag gta aat             1048
Asp Ile Glu Gly Ala Arg Glu Leu Gln Glu Lys Asn Gly Glu Val Asn
265                 270                 275                 280 tgt tta aat aca cgt tac agt gca aca aga ata gca gaa cat att gca             1096
Cys Leu Asn Thr Arg Tyr Ser Ala Thr Arg Ile Ala Glu His Ile Ala
                285                 290                 295 aaa gaa atg aag atg aag ata ttt aag aat att ata gaa gag aat gcc             1144
Lys Glu Met Lys Met Lys Ile Phe Lys Asn Ile Ile Glu Glu Asn Ala
            300                 305                 310 aaa atc tgt atc ata att gat gag gca tct aca gtt tca aag aaa acc             1192
Lys Ile Cys Ile Ile Ile Asp Glu Ala Ser Thr Val Ser Lys Lys Thr
            315                 320                 325 acc cta gtg att tat ctc cag tgc aca att cag tca gct cct gca cct             1240
Thr Leu Val Ile Tyr Leu Gln Cys Thr Ile Gln Ser Ala Pro Ala Pro
            330                 335                 340 gtt atg tta ttt gtg gct tta aaa gaa ttg gtg tca act ata gca gag             1288
Val Met Leu Phe Val Ala Leu Lys Glu Leu Val Ser Thr Ile Ala Glu
345                 350                 355                 360 tgt att gtc aat aca tta ttg act act tta aat gat tgt ggt ttt aca             1336
Cys Ile Val Asn Thr Leu Leu Thr Thr Leu Asn Asp Cys Gly Phe Thr
                365                 370                 375 aat gaa tat ttg aaa gca aat tta att gca ttt tgt tct gat ggt gct             1384
Asn Glu Tyr Leu Lys Ala Asn Leu Ile Ala Phe Cys Ser Asp Gly Ala
            380                 385                 390 aat aca anc ctg gga aga aag tct gga gta gct aca aaa ttg tta gaa             1432
Asn Thr Xaa Leu Gly Arg Lys Ser Gly Val Ala Thr Lys Leu Leu Glu
            395                 400                 405 aat ttt cct gaa atc atc att tgg aac tgt tta aat cat cga tta caa             1480
Asn Phe Pro Glu Ile Ile Ile Trp Asn Cys Leu Asn His Arg Leu Gln
410                 415                 420 ttg tca ctt gat gat tct ata tcc gaa ata aaa caa att aat cat tta             1528
Leu Ser Leu Asp Asp Ser Ile Ser Glu Ile Lys Gln Ile Asn His Leu
425                 430                 435                 440
```

-continued

```
ann tat aa                                                          1536
Xaa Tyr
```

<210> SEQ ID NO 6
<211> LENGTH: 442
<212> TYPE: PRT
<213> ORGANISM: Homo sapiens
<220> FEATURE:
<221> NAME/KEY: misc_feature
<222> LOCATION: (395)..(395)
<223> OTHER INFORMATION: The 'Xaa' at location 395 stands for Asn, Ser,
      Thr, or Ile.
<220> FEATURE:
<221> NAME/KEY: misc_feature
<222> LOCATION: (441)..(441)
<223> OTHER INFORMATION: The 'Xaa' at location 441 stands for Lys, Asn,
      Arg, Ser, Thr, Ile, or Met.

<400> SEQUENCE: 6

```
Met Gly Asp Pro Gly Ser Glu Ile Ile Glu Ser Val Pro Pro Ala Gly
1               5                   10                  15

Pro Glu Ala Ser Glu Ser Thr Thr Asp Glu Asn Glu Asp Asp Ile Gln
            20                  25                  30

Phe Val Ser Glu Gly Pro Ser Arg Pro Val Leu Glu Tyr Ile Asp Leu
        35                  40                  45

Val Cys Gly Asp Asp Glu Asn Pro Ser Ala Tyr Tyr Ser Asp Ile Leu
    50                  55                  60

Phe Pro Lys Met Pro Lys Arg Gln Gly Asp Phe Leu His Phe Leu Asn
65                  70                  75                  80

Met Lys Lys Val Lys Thr Asp Thr Glu Asn Asn Glu Val Ser Lys Asn
                85                  90                  95

His Cys Arg Leu Ser Lys Ala Lys Glu Pro His Phe Glu Tyr Ile Glu
            100                 105                 110

Gln Pro Ile Ile Glu Glu Lys Pro Ser Leu Ser Ser Lys Lys Glu Ile
        115                 120                 125

Asp Asn Leu Val Leu Pro Asp Cys Trp Asn Glu Lys Gln Ala Phe Met
    130                 135                 140

Phe Thr Glu Gln Tyr Lys Trp Leu Glu Ile Lys Glu Gly Lys Leu Gly
145                 150                 155                 160

Cys Lys Asp Cys Ser Ala Val Arg His Leu Gly Ser Lys Ala Glu Lys
                165                 170                 175

His Val His Val Ser Lys Glu Trp Ile Ala Tyr Leu Val Thr Pro Asn
            180                 185                 190

Gly Ser Asn Lys Thr Thr Arg Gln Ala Ser Leu Arg Lys Lys Ile Arg
        195                 200                 205

Glu His Asp Val Ser Lys Ala His Gly Lys Ile Gln Asp Leu Leu Lys
    210                 215                 220

Glu Ser Thr Asn Asp Ser Ile Cys Asn Leu Val His Lys Gln Asn Asn
225                 230                 235                 240

Lys Asn Ile Asp Ala Thr Val Lys Val Phe Asn Thr Val Tyr Ser Leu
                245                 250                 255

Val Lys His Asn Arg Pro Leu Ser Asp Ile Glu Gly Ala Arg Glu Leu
            260                 265                 270

Gln Glu Lys Asn Gly Glu Val Asn Cys Leu Asn Thr Arg Tyr Ser Ala
        275                 280                 285

Thr Arg Ile Ala Glu His Ile Ala Lys Glu Met Lys Met Lys Ile Phe
    290                 295                 300

Lys Asn Ile Ile Glu Glu Asn Ala Lys Ile Cys Ile Ile Ile Asp Glu
```

-continued

| | | | | 305 | | | | 310 | | | | 315 | | | | 320 |
|---|---|---|---|---|---|---|---|---|---|---|---|---|---|---|---|---|
| Ala | Ser | Thr | Val | Ser | Lys | Lys | Thr | Thr | Leu | Val | Ile | Tyr | Leu | Gln | Cys |
| | | | | 325 | | | | 330 | | | | 335 | | | |
| Thr | Ile | Gln | Ser | Ala | Pro | Ala | Pro | Val | Met | Leu | Phe | Val | Ala | Leu | Lys |
| | | | | 340 | | | | 345 | | | | 350 | | | |
| Glu | Leu | Val | Ser | Thr | Ile | Ala | Glu | Cys | Ile | Val | Asn | Thr | Leu | Leu | Thr |
| | | | | 355 | | | | 360 | | | | 365 | | | |
| Thr | Leu | Asn | Asp | Cys | Gly | Phe | Thr | Asn | Glu | Tyr | Leu | Lys | Ala | Asn | Leu |
| | | | 370 | | | | 375 | | | | 380 | | | | |
| Ile | Ala | Phe | Cys | Ser | Asp | Gly | Ala | Asn | Thr | Xaa | Leu | Gly | Arg | Lys | Ser |
| 385 | | | | | 390 | | | | 395 | | | | | 400 | |
| Gly | Val | Ala | Thr | Lys | Leu | Leu | Glu | Asn | Phe | Pro | Glu | Ile | Ile | Ile | Trp |
| | | | | 405 | | | | 410 | | | | 415 | | | |
| Asn | Cys | Leu | Asn | His | Arg | Leu | Gln | Leu | Ser | Leu | Asp | Asp | Ser | Ile | Ser |
| | | | | 420 | | | | 425 | | | | 430 | | | |
| Glu | Ile | Lys | Gln | Ile | Asn | His | Leu | Xaa | Tyr | | | | | | |
| | | | 435 | | | | 440 | | | | | | | | |